United States Patent
Hohlweg et al.

[11] Patent Number: 5,276,035
[45] Date of Patent: Jan. 4, 1994

[54] 1,4-DISUBSTITUTED PIPERAZINES

[75] Inventors: Rolf Hohlweg, Kvistgaard; Erling Guddal, Brondby; Erik B. Nielsen, V rlose, all of Denmark

[73] Assignee: Novo Nordisk A/S, Bagsvaerd, Denmark

[21] Appl. No.: 879,518

[22] Filed: May 4, 1992

Related U.S. Application Data

[63] Continuation of Ser. No. 728,493, Jul. 11, 1991, abandoned.

Foreign Application Priority Data

Jul. 26, 1990 [DK] Denmark .................. 1785/90

[51] Int. Cl.$^5$ .............. A61K 31/495; A61K 33/42; C07D 295/15; C07D 409/06
[52] U.S. Cl. .................... 514/252; 514/85; 514/255; 544/337; 544/367; 544/369; 544/379; 544/397; 548/237
[58] Field of Search ............... 544/337, 367, 369, 379, 544/397; 514/85, 252, 255

[56] References Cited

U.S. PATENT DOCUMENTS

| | | | |
|---|---|---|---|
| 2,988,551 | 6/1961 | Morren | 544/397 |
| 3,558,631 | 1/1971 | Kaiser et al. | 260/268 |
| 4,096,259 | 6/1978 | Buzas et al. | 544/397 |
| 4,766,215 | 8/1988 | Abov-Gharbia et al. | 544/316 |
| 4,866,062 | 9/1989 | Tóth et al. | 514/255 |
| 4,868,184 | 9/1989 | Tóth et al. | 514/255 |
| 4,874,765 | 10/1989 | Lapis et al. | 544/397 |
| 4,908,365 | 3/1990 | Buzas et al. | 544/397 |
| 4,973,591 | 11/1990 | Selkirk et al. | 514/255 |
| 5,177,077 | 1/1993 | Hohlweg et al. | 544/379 |

FOREIGN PATENT DOCUMENTS

| | | |
|---|---|---|
| 0099148 | 1/1984 | European Pat. Off. |
| 0157420 | 10/1985 | European Pat. Off. |
| 0285219 | 10/1988 | European Pat. Off. |
| 2276824 | 1/1976 | France |
| 2673182 | 8/1992 | France |
| 1529782 | 10/1978 | United Kingdom |
| 1545094 | 5/1979 | United Kingdom |

OTHER PUBLICATIONS

Rueger et al, Chemical Abstracts, vol. 111, No. 57757 (1989).
Jilek et al, Collect. Czech. Chem. Commun. 54, p. 2248 (1989).

Primary Examiner—Mukund J. Shah
Assistant Examiner—E. Bernhardt
Attorney, Agent, or Firm—Steve T. Zelson; Elias J. Lambiris

[57] ABSTRACT

A disubstituted piperazine compound having the formula

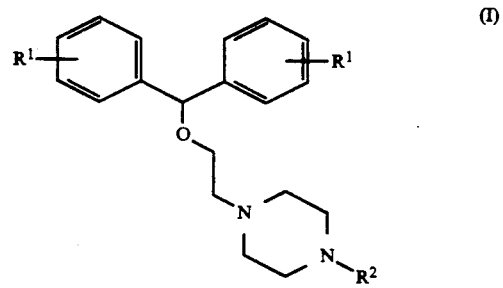

(I)

wherein $R^1$ is halogen, methoxy, $C_{1-6}$-alkyl or trifluoromethyl, and $R^2$ is methyl or substituted $C_{1-8}$-alkyl, $C_{3-8}$-alkenyl or $C_{3-8}$-cycloalkyl, where substituents may be hydroxy-, keto- or oximino-groups in any position leading to a stable tertiary amine; or $R^2$ is a straight or branched $C_{1-8}$-alkyl or $C_{3-8}$-alkenyl, which in any position may be substituted as above, but is terminally substituted with one of the following groups: cyano, optionally $C_{1-4}$-alkoxy-substituted $C_{1-4}$-alkoxy, dimethoxy, optiontionally substituted phenoxy, phosphonic acid, thienyl, furyl, oxazoline, isoxazole, oxadiazole, where the optional substitution is represented by $C_{1-6}$-alkyl or phenyl, provided that when cyano is the only substituent in $R^2$, $R^2$ must contain at least four carbon atoms, and pharmaceutically acceptable acid addition salts thereof.

The compounds are useful in the treatment of mental disorders in which a dopaminergic deficit is implicated.

15 Claims, No Drawings

1,4-DISUBSTITUTED PIPERAZINES

This application is a continuation application of co-ending application Ser. No. 07/728,493, filed Jul. 11, 1991 now abandoned.

This invention concerns novel diarylalkoxyalkylpiperazines useful for their inhibitory activity at dopamin uptake sites, a method of preparing the same, pharmaceutical compositions containing them and their use for treating mental disorders as e.g. depression and other CNS-related diseases as Parkinson's disease.

Benzhydrylpiperazines, where the benzhydryl group is connected to the nitrogen of a piperazine over a —O—(CH$_2$)n— moiety, are known from the German patent publication No. DOS 2719246, where spasmolytic and antiemetic activity is claimed while EP patent appl. Nos. 157420 and 285219 claim lipoxygenase inhibiting and sleep improving properties respectively. Furthermore, in U.S. Pat. No. 4,766,215 and European patent application No. 0254627 similar benzhydrylethers are described as antihistaminic compounds; German patent publication No. DE 3726068 claims calcium antagonistic activity for compounds with the aforementioned general structure. Other compounds with the mentioned general structure are also described in European patent application Nos. 0243903, 0243904, 0243905, in GB Patent No. 1545094 and Dutch patent appl. No. NL 8202636 and claimed to be useful in case of degeneration or hypofunction of the dopaminergic system.

In U.S. Pat. No. 4,096,259, similar compounds bearing polar carboxyl- or alkoxycarbonyl groups are described as central stimulants, however, no dopaminergic activity is claimed or evident from the patent description.

Generally the compounds mentioned in the different patent sspecifications vary greatly with reference to the substitution of the second piperazine nitrogen and thus may give rise to the great variety in pharmacological activity.

It has now unexpectedly been found that by introducing a substituent containing certain polar groups in the 4-position of the aforementioned piperazine compounds, new and novel compounds with greatly improved in vivo activity can be obtained. It is expected that such substances possess antidepressant, antiparkinson, antipsychotic, antispastic, memory enhancing, as well as other similarly useful therapeutic effects in diseases in which a dopaminergic deficit is implicated. The substances may also have beneficial effects against drug craving or drug abuse.

The compounds of the invention have the general formula I:

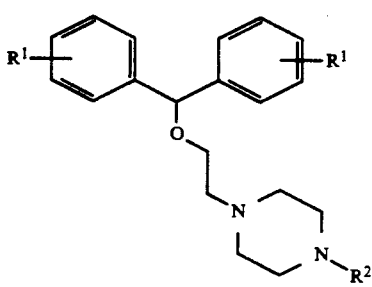

wherein R$^1$ is halogen, methoxy, C$_{1-6}$-alkyl or trifluoromethyl, and R$^2$ is methyl or substituted C$_{1-8}$-alkyl, C$_{3-8}$-alkenyl or C$_{3-8}$-cycloalkyl, where substituents may be hydroxy-, keto- or oximino-groups in any position leading to a stable tertiary amine; or R$^2$ is a straight or branched C$_{1-8}$-alkyl or C$_{3-8}$-alkenyl, which in any position may be substituted as above, but is terminally substituted with one of the following groups: cyano, optionally C$_{1-4}$-alkoxy-substituted C$_{1-4}$-alkoxy, dimethoxy, optionally substituted phenoxy, phosphonic acid, thienyl, furyl, oxazoline, isoxazole, oxadiazole, where the optional substitution is represented by C$_{1-6}$-alkyl or phenyl, provided that when cyano is the only substituent in R$^2$, R$^2$ must contain at least four carbon atoms, and pharmaceutically acceptable acid addition salts thereof.

The compounds of formula I may exist as geometric and optical isomers and all isomers and mixtures thereof are included herein. Isomers may be separated by means of standard methods such as chromatographic techniques or fractional crystallization of suitable salts.

Pharmaceutically acceptable acid addition salts of compounds of formula I include those derived from inorganic or organic acids such as hydrochloric, hydrobromic, sulfuric, phosphoric, acetic, lactic, maleic, phthalic and fumaric acid.

The invention also relates to a method of preparing the above mentioned compounds. This method comprises:

a) reacting a compound of formula II

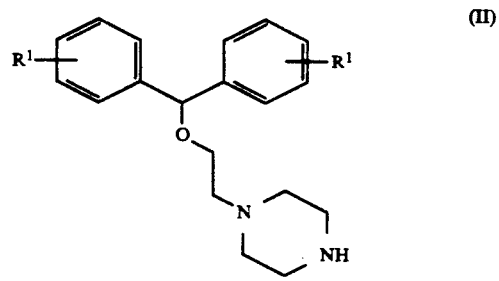

where R$^1$ has the meaning defined above with a reactive reagent containing the group R$^2$ as defined above, or groups that may be converted to group R$^2$ by generally known methods.

Generally known methods for alkylating secondary amines are for example:

1) reaction of the monosubstituted piperazine of formula II with an alkyl halide or tosylate.

2) addition of the monosubstituted piperazine compound of formula II to a reactive double bond or epoxide.

3) acylation of the monosubstituted piperazine compound of formula II by known methods followed by reduction to yield the desired tertiary amine of formula I.

b) reacting a compound of formula III

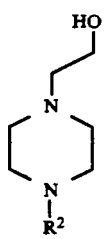

(III)

prepared by alkylation of 1-(2-hydroxyethyl)-piperazine according to one of the aforementioned methods, and thereafter combining this disubstituted piperazine with a compound of formula V

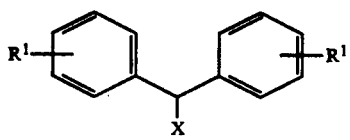

(V)

where R¹ has the meaning mentioned above, and X means OH or halogen, applying standard methods of ether synthesis, consisting in a condensation reaction with the removal of water or halogen halide.

c) reacting a compound of the formula IV

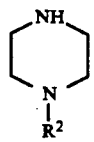

(IV)

prepared by alkylating piperazine according to generally well known methods such as described in section a) and b) above for introducing the group R², with an optionally substituted diarylmethoxyethyl derivative of formula VI

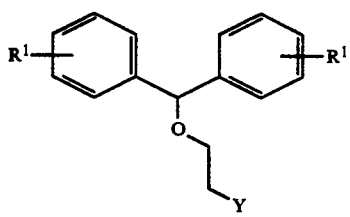

(VI)

where R¹ has the meaning as defined above and Y means halogen to obtain the desired compound of formula I.

The biological properties of the compounds according to the invention can be illustrated in the following way:

Biochemistry

Test 1

The compounds were tested for their ability to inhibit the binding of 3H-GBR 12935 to the DA-uptake complex in a striatal membrane preparation following the method described by Andersen (Eur.J.Pharmacol. 166: 493-504, 1989).

PHARMACOLOGY

The compounds were also tested for their ability to increase the motility of mice following intravenous administration using the method outlined below.

Test 2

Subjects

Male NMRI mice are used (20±2 g). The animals are housed 20-30 per cage under constant temperature (20±1° C.) and relative humidity (40-60%). The animals are brought into the experimental room in the afternoon, the day before they undergo testing.

METHODS

The experimentally-naive, uninjected mice are acclimatized by being placed in a plexiglass box (WLH: 20×20×38 cm), four per box, for a 120 min period, and then injected with the test compound whereafter they are replaced in the plexiglass box.

The plexiglass box is equipped with a frame of photocells (spaced equidistantly) which are situated so as to detect locomotor behaviour of the animals (1 cm above the floor). The photocell chamber is housed in an sound-insulated, dimly-lit, ventilated chest. As a measure of exploratory behaviour, the number of photocell crossings in a 360 min period is detected using a minicomputer. Testing is made between 7:00 and 17.00 h.

DRUG TESTING

Drugs are injected i.v. simultaneously with start of testing; N=4/dose; 4-5 doses of test drug is given in a volume of 10 ml/kg.

RESULTS

Computer programmed log-probit methods are used to generate an $ED_{50}$ in mg/kg using as minimum the control result, and as maximum values are used 7700 (this latter value has been experimentally found as the maximum motility counts after d-amphetamine in a 20 min period).

The test result is the lowest $ED_{50}$ value determined at a 20 min interval during the 360 min test period.

The present invention relates to the increase in the ratio between in vitro inhibition of 3H-GBR 12935 binding and the in vivo activity in the increasing motility. Thus, a reference compound such as GBR 12909 had a ratio of only 3.2, whereas for the compounds described in examples 10 and 13 the ratios were increased to 7.5 and 7.4, respectively. Thus, the compounds had higher in vivo activity than can be expected when comparing with GBR 12909.

Test results obtained by testing some compounds of the invention appears from the following table I:

TABLE 1

| Compound | Test 1 (nm) | Test 2 (mg/kg) | Ratio |
| --- | --- | --- | --- |
| Example 10 | 18 | 2.4 | 7.5 |
| Example 13 | 20 | 2.7 | 7.4 |
| GBR 12909 | 7.5 | 2.3 | 3.2 |

The pharmaceutical preparations or compositions comprising the compounds of the invention may be administered to humans or animals by oral or parenteral route.

An effective amount of the active compound or a pharmaceutically-acceptable salt thereof may be determined in accordance with the usual factors, such as the nature and severity of the condition and the weight of the mammal requiring treatment.

Conventional excipients are such pharmaceutically-acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose, and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances and the like, which do not deleteriously react with the active compounds.

Injectable solutions or suspensions, preferably aqueous solutions with the active compound dissolved in polyhydroxylated castor oil, are particularly suitable for parenteral administration.

Ampoules are convenient unit dosage forms.

Tablets, dragees, or capsules containing talc and/or a carrier or binder or the like are particularly suitable for oral administration. The carrier preferably is lactose and/or corn starch and/or potato starch.

A syrup, elixir, or the like can be used in the cases where a sweetened vehicle can be employed or is desired.

Generally, the compounds of this invention are dispensed in unit dosage form comprising 50-200 mg of active ingredient in or together with a pharmaceutically-acceptable carrier per unit dosage.

The dosage of the compounds according to this invention is 1-500 mg/day, e.g., about 100 mg per dose, when administered to patients, e.g., humans, as a drug.

A typical tablet which may be prepared by conventional tabletting techniques contains:

| Core: | |
| --- | --- |
| Active compound (as free compound or salt thereof) | 100 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | 1 mg |
| Coating: | |
| HPMC | approx. 9 mg |
| *Mywacett ® 9-40 T | approx. 0.9 mg |

*Acylated monoglyceride used as plasticizer for film-coating

The compounds of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical composition and unit dosage forms thereof may comprise conventional ingredients in conventional proportions, with or without additional active compounds or principles, and such unit dosage forms may contain any suitable effective DA-uptake inhibitory amount of the active ingredient commensurate with the intended daily dosage range to be employed. Tablets containing fifty (50) milligrams of active ingredient or, more broadly, ten (10) to two hundred (200) milligrams, per tablet, are accordingly suitable representative unit dosage forms.

Due to their high degree of DA-uptake inhibitory activity and their low toxicity, together presenting a most favorable therapeutic index, the compounds of the invention may be administered to a subject, e.g., a living animal body, in need of such treatment, elimination, alleviation, or amelioration of an indication which is sensitive to a change in the neuronal reuptake of dopamine, often preferably in the form of a non-toxic acid addition salt thereof, e.g. a hydrohalide, especially hydrochloride and hydrobromide, or a sulfate, nitrate, phosphate and the like, or an organic salt as acetate, propionate, lactate, malonate, succinate, maleate, fumarate, citrate and the like, concurrently, simultaneously, or together with a pharmaceutically- acceptable carrier or diluent, especially and preferably in the form of a pharmaceutical composition thereof, whether by oral, rectal, or parenteral (including subcutaneous) route, in an effective amount. Suitable dosage ranges are 50-200 milligrams daily, preferably 50-100 milligrams daily, and especially 70-100 milligrams daily, depending as usual upon the exact mode of administration, form in which administered, the indication toward which the administration is directed, the subject involved and the body weight of the subject involved, and the preference and experience of the physician or veterinarian in charge. Such method of treating may be described as the treatment of an indication caused by or related to the dopamine-system in a subject in need thereof, which comprises the step of administering to the said subject a neurologically- or neuroleptically-effective amount of a DA-uptake inhibitory compound of the invention.

The invention will now be described in further detail with reference to the following examples.

EXAMPLE 1

1-(2-[bis-(4-fluorophenyl)methoxy]ethyl)-4-[3-(3-thienyl)propenyl]piperazine

To a solution of 1.7 g (0.0051 mol) 1-(2-[bis(4-fluorophenyl)methoxy]ethyl)piperazine, U.S. Pat. No. 1545094, in a mixture of 10 ml toluene and 10 ml pyridine, 0.86 g (0.0050 mol) 3-(3-thienyl)propenoyl chloride, dissolved in 5 ml toluene, were added dropwise at room temperature.

The mixture was refluxed for 0.5 h, cooled, diluted with 100 ml toluene and successively washed with a 1N sodium hydroxide solution, 2 portions of water and brine. Evaporation of the toluene phase in vacuo gave 2.46 g of the intermediate 1-(2-[bis(4-fluorophenyl)methoxy]ethyl)-4-[3-(3-thienyl)-1-oxo-2-propenyl]piperazine as a dark oil.

This was dissolved in 20 ml of dry diethyl ether and added dropwise to a suspension of 0.48 g (0.0127 mol) lithium aluminium hydride in 30 ml of dry diethyl ether. The mixture was then heated to reflux for 1 h, cooled and hydrolyzed with a mixture of water and tetrahydrofuran. The solids were filtered off and to the filtrate was added an excess of a solution of maleic acid in diethyl ether. The precipitate was collected by filtration and recrystallized from methanol/isopropanol. Yield 0.80 g (23%) of the title compound as the dimaleate salt. M.p. 182°-85° C.

NMR (400 MHz) in DMSO-d$_6$ [ppm]: 2.6-3.5 (m) 10H; 3.56 (m) 4H; 5.55 (s) 1H; 6.15 (m) 5H; 6.75 (d) 1H; 7.20 (t) 4H; 7.40 (m) 5H; 7.57 (m) 2H.

Calculated for C$_{34}$H$_{35}$F$_2$N$_2$O$_9$S: C 59.47%, H 5.28%, N 4.08%.

Found: C 59.69%, H 5.27%, N 3,97%.

EXAMPLE 2

1-(2-[bis-(4-fluorophenyl)methoxy]ethyl)-4-(2-hydroxyethyl)piperazine

To a refluxing mixture of 1.05 g (0.0081 mol) N-(2-hydroxy-ethyl)piperazine, 0.75 g (0.0054 mol) dry potassium carbonate and 5 ml toluene, a solution of 0.76 g (0.0027 mol) 1-[(2-chloroethoxy)(4-fluorophenyl)methyl]-4-fluorobenzene in 3 ml toluene was added dropwise. The reaction mixture was refluxed for 11 h and then cooled to room temperature. It was diluted with toluene (100 ml) and extracted with 2N hydrochloric acid (100 ml). The acidic extract was washed with one portion of toluene, then rendered basic by addition of 4N sodium hydroxide solution (75 ml) and extracted with toluene (100 ml). The toluene solution was washed successively with two portions of water and once with brine. Evaporation in vacuo gave a yellowish oil, which was redissolved in acetonitrile (20 ml). The title compound was precipitated as the dimaleate salt with an excess of a maleic acid solution in acetonitrile. By recrystallization from hot acetonitrile/methanol 1.29 g (78% of the theoretical yield) of the title compound was obtained as white crystals, m.p. 163° C.

NMR (400 MHz) in DMSO-d$_6$ [ppm] 2.6-3.4 (m) 12H; 3.52 (t) 2H; 3.70 (t) 2H; 5.2 (s) 1H; 5.54 (s) 1H; 6.17 (s) 4H; 7.20 (t) 4H; 7.40 (dd) 4H.

Calculated for C$_{29}$H$_{34}$F$_2$N$_2$O$_{10}$: C 57.22, H 5.64, N 4.60%.

Found: C 57,37, H 5.72, N 4.83%.

In the same manner was prepared:

1-(2-[Bis-(2-methylphenyl)methoxy]ethyl)-4-(2-hydroxyethyl)piperazine, dimaleate White crystals, m.p. 170°-71° C.

NMR (400 MHz) in DMSO-d$_6$ (ppm): 2.25 (s) 6H; 2.6-3.4 (m) 14H; 3.58 (t) 2H; 3.68 (t) 2H; 5.72 (s) 1H; 6.15 (s) 4H; 7.05-7.25 (m) 8H.

Calculated for C$_{31}$H$_{40}$N$_2$O$_{10}$: C 61.99, H 6.71, N 4.66%.

Found: C 62.39, H 6.81, N 4.54%.

EXAMPLE 3

1-(2-[bis-(4-fluorophenyl)methoxy]ethyl)-4-methyl-piperazine

To a refluxing mixture of 4.2 g (0.042 mol) N-methyl-piperazine, 3.9 g (0.028 mol) potassium carbonate and 25 ml toluene, a solution of 4.0 g (0.014 mol) 1-[(2-chloroethoxy)(4-fluorophenyl)methyl]-4-fluorobenzene in 25 ml toluene was added dropwise. The reaction mixture was refluxed for 48 h and then cooled to room temperature. It was diluted with toluene (100 ml), washed with water and extracted with a 10% aqueous solution of tartaric acid. The acidic extract was washed once with toluene, then rendered basic by addition of 4N sodium hydroxide solution and extracted with toluene. The toluene solution was washed successively with two portions of water and once with brine. Evaporation in vacuo gave 3.44 g of a brown oil, which was redissolved in diethyl ether and precipitated with gaseous hydrogen chloride. The precipitate was collected by filtration and recrystallilzed from isopropanol. 3.12 g (53% of the theoretical yield) of the title compound as the dihydrochloride was obtained. M.p. 161°-62° C.

NMR (400 MHz) in DMSO-d$_6$ [ppm]: 2.8 (s) 3H; 3.2-4.0 (m) 12H; 5.6 (s) 1H; 7.2 (t) 4H; 7.5 (dd) 4H.

Calculated for C$_{20}$H$_{26}$F$_2$N$_2$OCl$_2$: C 57.28, H 6.26, N 6.68%.

Found: C 57.57, H 6.38, N 6.61%.

EXAMPLE 4

1-(2-[bis(4-fluorophenyl)methoxy]ethyl)-4-[4-oxo-4-(2-thienyl)butyl]piperazine

A mixture of 1.67 g (0.005 mol) 1-(2-[bis(4-fluorophenyl)-methoxy]ethyl)piperazine, (U.S. Pat. No. 1545094), 1.89 g (0.010 mol) 3-chloropropyl-2-thienyl ketone, 1.52 g (0.011 mol) potassium carbonate and 30 ml methylisobutyl ketone was stirred and heated to reflux for 45 h. The reaction mixture was then evaporated in vacuo. The residue was redissolved in dichloromethane (1 00 ml) and washed twice with water (100 ml). The organic layer was then separated and dried with sodium sulfate. Evaporation in vacuo left a brown syrup. This was redissolved in dry ether and precipitated as the dihydrochloride with gaseous hydrogen chloride. The precipitate was collected by filtration and recrystallized from isopropanol. White crystals, m.p. 185°-88° C. (0.98 g=35%).

NMR (400 MHz) in DMSO-d$_6$ [ppm]: 2.03 (m) 2H; 3.0-4.2 (m) 16H; 5.60 (s) 1H; 7.18 (t) 4H; 7.27 (t) 1H; 7.50 (dd) 4H; 8.00 (d) 1H; 8.04 (d) 1H.

Calculated for C$_{27}$H$_{32}$Cl$_2$F$_2$N$_2$O$_2$S: C 58.17, H 5.79, N 5.02%.

Found: C 58.47, H 5.91, N 4.94%.

EXAMPLE 5

1-(2-[bis(4-fluorophenyl)methoxy]ethyl)-4-[4-hydroxy-4-(2-thienyl)butyl]piperazine 100 mg (0.00264 mol) sodium borohydride was added to a stirred solution of 0.72 g (0.00149 mol) 1-(2-[bis(4-fluorophenyl)methoxy]ethyl)-4-[4-oxo-4-(2-thienyl)-butyl]piperazine (as described in example 4) in 8 ml ethanol. The reaction mixture was refluxed for 1 h, and then cooled and evaporated in vacuo. The residue was redissolved in diethyl ether, washed twice with water and once with brine. The ether solution was dried with sodium sulfate and the filtered solution treated with gaseous hydrogen chloride in excess. The precipitate was recrystallized from methanol, yielding the title compound as the dihydrochloride, m.p. 192°-93° C.

NMR (400 MHz) in DMSO-d$_6$ [ppm]1.7 (m) 4H; 3.0-4.2 (m) 15H; 4.80 (t) 1H; 5.60 (s) 1H; 7.0 (m) 2H; 7.2 (t) 4H; 7.4 (t) 1H; 7.5 (dd) 4H.

Calculated for C$_{27}$H$_{34}$Cl$_2$F$_2$N$_2$O$_2$S: C 57.96, H 6.12, N 5.01%.

Found: C 58.41, H 6.30, N 5.00%.

EXAMPLE 6

1-(2(bis-(4-fluorophenyl)-methoxy)-ethyl)-4-(3,5-dimethylisoxazole-4-yl)-methyl-piperazine 1 66 g (5 mM) of 1-(2-(bis((4-fluorophenyl)-methoxy)ethyl)piperazine was dissolved in 5 ml of dry dimethylformamide, 3.46 g of potassium carbonate was added, and a solution of 1.09 g (7.5 mM) of 4-chloromethyl-3,5-dimethyl-isoxazole in 5 ml of dry dimethylformamide was added dropwise. After 45 min. at 25° C. 20 ml of toluene and 20 ml of water were added. The phases were separated, the aqueous phase extracted with toluene, and the toluene phases were washed with water, dried and evaporated. The residue was dissolved in 25 ml of acetone, and 10 mM of hydrogen chloride dissolved in acetone were added. The precipitated white crystals were isolated by filtration. They melted at 220°-228° C. and showed H-NMR spectrum in accordance with the dihydrochloride of the title compound.

NMR-data (CDCl$_3$) ppm: 2.2 (s) 3H; 2.3 (s) 3H; 2.4-2.6 (m) 8H; 2.7 (t) 2H; 3.2 (s) 2H; 3.6 (t) 2H; 5.3 (s) 1H; 7.0 (t) 4H; 7.3 (dd) 4H.

| Microanalysis | C | H | N | Cl |
|---|---|---|---|---|
| Calculated for $C_{25}H_{31}N_3O_2F_2Cl_2$ | 58.37 | 6.07 | 8.17 | 13.78 |
| Found | 58.44 | 6.15 | 8.02 | 13.70 |
|  | 58.49 | 6.09 | 8.07 | 13.69 |

EXAMPLE 7

1-(2(bis-(4-fluorophenyl)-methoxy)-ethyl)-4-(3-(4,4-dimethyl-oxazoline-2-yl)-propyl-piperazine Step A:

17.8 g (0.2 M) of 2-amino-2-methyl-propanol was dissolved in 50 ml of methylene chloride, cooled to 0° C. and 14.1 g (0.1M) of 4-chlorobutyryl chloride dissolved in 50 ml of methylene chloride was added dropwise. The precipitated amine hydrochloride was removed by filtration and the solvent removed in vacuo. The residue was treated with 21.8 ml (0.3M) of thionyl chloride in a strongly exothermic reaction. The reaction mixture was stirred for 1 h, in which time the temperature dropped to 25° C. The excess of thionyl chloride was evaporated in vacuo, the residue dissolved in tetrahydrofuran and treated with 28 ml triethylamine. The precipitated amine hydrochloride was removed by filtration, the filtrate concentrated and distilled in vacuo to yield 7.5 g of an oil boiling at 38°42° C. (0.03 mm), showing H-NMR spectrum in accordance with 2-(3-chloropropyl)-4,4-dimethyloxazoline Step B:

1.86 g (10 mM) of 2-(3-chloropropyl)-4,4-dimethyl-oxazoline as prepared in Step A and 1.66 g (5 mM) of 1-(2-(bis-(4-fluorophenyl)-methoxy)-ethyl)-piperazine were dissolved in 5 ml of dry dimethylformamide, 3.46 g of potassium carbonate and 0.86 g of potassium iodide were added, and the mixture heated to 120° C. for 1 h and left at 25° C. for 16 h. 20 ml of toluene and 20 ml of water were added, and after the phases were separated, the toluene phase was washed with water and the aqueous phase extracted twice with toluene. The solvent was removed, the residue dissolved in 13 ml of ethanol and treated with 2.7 ml of a 4.58N solution of hydrogen chloride in ether. The hydrochloride salt was precipitated by addition of 25 ml of ether at 0° C. The isolated crystals were reprecipitated in ethanol/ether to yield white crystals melting at 135°-150° C., and showing H-NMR spectrum in accordance with the title compound. Microanalysis indicated a composition corresponding to a trihydrochloride monohydrate:

| Microanalysis | C | H | N | Cl | KF |
|---|---|---|---|---|---|
| Calculated for $C_{27}H_{40}N_3O_3F_2Cl_3$ | 54.14 | 6.73 | 7.02 | 17.76 | 3.33 |
| Found | 53.70 | 6.69 | 6.96 | 17.46 | 3.43 |
|  | 53.55 | 6.64 | 6.98 | 17.32 | 3.60 |

(KF means Karl Fischer water determination).

EXAMPLE 8

1-(2-(bis-(4-fluorophenyl)-methoxy)-ethyl(-4-(6-hydroxyhexyl)-piperazine 700 mg (2.1 mM) of 1-(2-(bis-(4-fluorophenyl)-methoxy)ethyl)piperazine was dissolved in 7 ml of dry dimethylformamide, 570 mg (3 mM) of 6-bromohexanol and 580 mg of potassium carbonate was added, and the mixture was heated at 120° C. for 30 min. 20 ml of toluene and 20 ml of water were added, the aqueous phase extracted with toluene, the toluene extracts were washed with water and evaporated to yield 800 mg of an oil. This oil was dissolved in ethanol, treated with charcoal (Norit SU 18), filtered and treated with 487 mg of maleic acid dissolved in 3 ml of ethanol. The precipitated crude dimaleate salt was redissolved in 10 ml of butanol and 10 ml of water, pH adjusted to 11 with base, and the butanol phase was evaporated in vacuo. The residual oil (618 mg) was dissolved in 15 ml of ether, and the dihydrochloride salt of the title compound was precipitated by addition of 1 ml of a 4,7N solution of hydrogen chloride in ether. The precipitated colourless crystals melted at 158°-160° C., and showed H-NMR spectrum and microanalysis in accordance with the proposed structure.

NMR-data DMSO)ppm: 1.2 (m) 8H; 1.4 (m) 2H; 1.6 (m) 2H; 2.8 (m) 2H; 2.9 (m) 2H; 2.8-3.3 (m) 8H (+H$_2$O); 3.4 (t) 2H; 3.5 (t) 2H; 5.5 (s) 1H; 6.2 (s) 4H; 7.2 (t) 4H; 7.4 (dd) 4H.

| Microanalysis | C | H | N | Cl |
|---|---|---|---|---|
| Calculated for $C_{25}H_{36}N_2O_2F_2 \cdot 2HCl$ | 59.64 | 7.21 | 5.57 | 14.08 |
| Found | 58.72 | 7.19 | 5.31 | 13.84 |
|  | 58.88 | 7.20 | 5.45 | 13.89 |

EXAMPLE 9

1-(2-(bis-(4-fluorophenyl)-methoxy)-ethyl)-4(8-hydroxyoctyl)-piperazine 700 mg (2.1 mM) of 1-(2-(bis-(4-fluorophenyl)-methoxy)ethyl)piperazine was dissolved in 7 ml of dry dimethylformamide, 660 mg (3 mM) of 8-bromooctanol and 580 mg of potassium carbonate were added, and the mixture was heated at 120° C. for 30 min. 20 ml of toluene and 20 ml of water were added, the aqueous phase extracted with toluene, and the combined toluene extracts were washed twice with water and evaporated to yield 870 mg of crude oil. This oil was dissolved in 10 ml of ethanol and treated with 487 mg of maleic acid dissolved in 5 ml of ethanol. The precipitated colourless crystals were isolated by filtration. They melted at 166°-167° C., and showed H-NMR spectrum and microanalysis in accordance with the dimaleate salt of the title compound.

NMR-data (DMSO)ppm: 1.3 (m) 8H; 1.4 (m) 2H; 1.6 (m) 2H; 2.5-3.3 (m) 12H (+H$_2$O); 3.4 (t) 2H; 3.5 (m) 2H; 5.5 (s) 1H; 6.6 (s) 4H; 7.2 (t) 4H; 7.4 (dd) 4H.

| Microanalysis | C | H | N |
|---|---|---|---|
| Calculated for $C_{35}H_{46}N_2O_{10}F_2$ | 60.55 | 6.68 | 4.04 |
| Found | 60.37 | 6.73 | 3.83 |
|  | 60.48 | 6.75 | 3.85 |

EXAMPLE 10

1-[2-(bis-(4-fluorophenyl)-methoxy)-ethyl]-4-(4-cyanobutyl)-piperazine 1.0 g (3 mM) of 1-[2-bis(4-fluorophenyl)-methoxy)-ethyl]piperazine was dissolved in 10 ml of dry dimethylformamide, 731 mg (4.5 mM) of 5-bromovaleronitrile and 830 mg of potassium carbonate were added, and the stirred mixture heated to 100° C. After 45 min. at 100° the reaction was completed as monitored by TLC (SiO$_2$/MeOH). To the cooled mixture 50 ml of water and 25 ml of toluene were added, the aqueous phase was extracted three times with toluene, the combined organic phases were washed with water and evaporated to yield 1.3 g of yellow oil. This crude product was dissolved in ether, and 1.3 ml of a 4.7N solution of HCl in ether was added. The crystalline precipitate was redissolved in water, washed twice with methylene chloride, pH adjusted to 12 with NaOH and the product was extracted with methylene chloride.

Reprecipitation from ether with HCl yielded 510 mg of white crystals, melting at 187°-9° C., and showing H-NMR in accordance with the dihydrochloride of the title compound.

NMR-data (DMSO) ppm: 1.6 (m) 2H; 1.8 (m) 2H; 2.6 (t) 2H; 3.1–3.8 (m) 14H (+H$_2$O); 5.6 (s) 1H; 7.2 (t) 4H; 7.5 (dd) 4H.

| Microanalysis | C | H | N | Cl |
|---|---|---|---|---|
| Calculated for C$_{24}$H$_{29}$N$_3$OF$_2$.2HCl | 59.26 | 6.42 | 8.64 | 14.58 |
| Found | 59.24 | 6.52 | 8.49 | 14.35 |
|  | 59.23 | 6.48 | 8.59 | 14.50 |

EXAMPLE 11

1-[2-(bis(4-fluorophenyl)-methoxy)ethyl]4-(3-cyanopropyl)piperazine

This compound was prepared by the general procedure as described in example no. 10, starting from 4-bromobutyronitrile, and isolated as the dihydrochloride crystallized from ethanol as white crystals melting at 137°-139° C., showing H-NMR spectrum in accordance with the title compound.

NMR-data (CDCl$_3$) ppm: 1.8 (m) 2H; 2.4–2.6 (m) 12H; 2.7 (t) 2H; 2.2 (m) 1H; 5.34 (s) 1H; 7.0 (t) 4H; 7.3 (dd) 4H; 3.55 (m) 3H.

| Microanalysis | C | H | N | Cl |
|---|---|---|---|---|
| Calculated for C$_{23}$H$_{27}$N$_3$OF$_2$.2HCl | 63.36 | 6.47 | 9.64 | 8.13 |
| Found | 63.36 | 6.58 | 10.01 | 8.38 |
|  | 63.08 | 6.50 | 9.95 | 8.46 |

In the same manner was prepared:

1-(2-[Bis-(4-fluorophenyl)methoxy]ethyl)-4-(5-cyanopentyl)piperazine, dimaleate

White crystalline powder, m.p. 175°-76° C.

NMR (400 MHz) in DMSO-d$_6$ (ppm): 1.37 (m) 2H; 1.60 (m) 4H; 2.6–3.4 (m) 14H; 3.53 (m) 2H; 5.53 (s) 1H; 6.18 (s) 4H; 7.18 (t) 4H; 7.38 (dd) 4H.

Calculated for C$_{33}$H$_{38}$N$_3$O$_9$F$_2$: C 60.08, H 5.96,N 6.37%.

Found: C 60.04, H 6.00,N 6.11%.

1-(2-[Bis-(4-fluorophenyl)methoxy]ethyl)-4-(7-cyanoheptyl)piperazine, dimaleate

White crystalline powder, m.p. 164°-65° C.

NMR (400 MHz) in DMSO-d$_6$ (ppm): 1.2–1.4 (m) 6H; 1.55 (m) 4H; 2.6–3.6 (m) 16H; 5.50 (s) 1H; 6.15 (s) 4H; 7.18 (t) 4H; 7.38 (dd) 4H.

Calculated for C$_{35}$H$_{43}$N$_3$O$_9$F$_2$: C 61.13, H 6.30, N 6.11%.

Found: C 60.85, H 6.30,N 5.94%.

EXAMPLE 12

1-[2-(bis-(4-fluorophenyl)-methoxy)ethyl]-4-(4-hydroxybutyl)piperazine

This compound was prepared by treating 1-[2-(bis-(4-fluorophenyl)-methoxy)-ethyl]-4-(3-ethoxycarbonylpropyl)piperazine (described in U.S. Pat. No. 4,096,259) with 1.8 equivalents of LiAlH$_4$ in refluxing tetrahydrofuran, the progress of the reaction being monitored by TLC. After standard workup the compound was isolated as a dimaleate salt, white crystals crystallized from ethanol, m.p. 166°-167° C. The H-NMR spectrum was in accordance with the title compound.

NMR-data (DMSO) ppm: 1.4 (m) 2H; 1.6 (m) 2H; 2.6–3.8 (m) 16H (+H$_2$O); 5.5 (s) 1H; 6.15 (s) 4H; 7.2 (t) 4H; 2.4 (dd) 4H.

| Microanalysis | C | H | N |
|---|---|---|---|
| Calculated for C$_{31}$H$_{38}$N$_2$O$_{10}$F$_2$ | 58.48 | 6.01 | 4.40 |
| Found | 58.46 | 6.06 | 4.50 |
|  | 58.63 | 6.11 | 4.57 |

EXAMPLE 13

1-[2-(bis-(4-fluorophenyl)-methoxy]-ethyl]-4-(2-hydroxypropyl)piperazine 635 mg (1.9 mM) of 1-(2-(bis-(4-fluorophenyl)-methoxy)-ethyl)-piperazine was dissolved in 2 ml of propylene oxide, and the mixture refluxed for 20 h, monitoring the conversion by TLC (MeOH). The propylene oxide was removed in vacuo, the residue dissolved in ethanol, filtered and 442 mg of maleic acid was added. The precipitate was collected after 16 h, and recrystallized from acetonitrile to produce a dimaleate melting at 171° C., showing H-NMR spectrum in accordance with the title compound.

NMR-data (DMSO) ppm: 1.1 (d) 3H; 2.6–3.4 (m) 12H (+H$_2$O); 3.5 (m) 2H; 4.0 (m) 1H; 5.2 (m) 1H; 5.5 (s) 1H; 6.2 (s) 4H; 7.2 (t) 4H; 7.4 (dd) 4H.

| Microanalysis | C | H | N |
|---|---|---|---|
| Calculated for C$_{30}$H$_{36}$N$_2$O$_9$F$_2$ | 57.90 | 5.83 | 4.20 |
| Found | 57.21 | 5.76 | 4.38 |

EXAMPLE 14

1-[2-(bis-(4-fluorophenyl)-methoxy)-ethyl]-4-(2,2-dimethoxyethyl)piperazine 1 06 g (3.2 mM) of 1-[2-(bis-(-4-fluorophenyl)methoxy)ethyl]-piperazine and 0.75 ml (4.8 mM) of bromoacetaldehyde dimethylacetal were dissolved in 5 ml of dry dimethylformamide, 1.32 g of potassium carbonate was added, and the mixture heated to reflux for 16 h. To the cooled mixture 25 ml of water and 15 ml of toluene were added, the aqueous phase was extracted three times with toluene, and the combined toluene phases were washed twice with water and evaporated to yield 1.3 g of oil, which was dissolved in ethanol and treated with 743 mg of maleic acid. The crystalline precipitate was collected and recrystallized from acetonitrile twice to yield white crystals melting at 171°–172° C. and showing H-NMR spectrum in accordance with the dimaleate salt of the title compound.

NMR-data (DMSO) ppm: 2.6–3.5 (m) 20H (+H$_2$O); 3.3 (s) 6H; 3.6 (m) 2H; 2.6 (m) 1H; 5.5 (s) 1H; 6.2 (s) 4H; 7.2 (t) 4H; 7.4 (dd) 4H.

| Microanalysis | C | H | N |
|---|---|---|---|
| Calculated for C$_{31}$H$_{43}$N$_2$O$_{11}$F$_2$ | 57.04 | 5.87 | 4.29 |
| Found | 57.24 | 5.91 | 4.17 |
| | 57.14 | 5.94 | 4.18 |

EXAMPLE 15

1-[2-(bis-(4-fluorophenyl)-methoxy)-ethyl]-4-(2-hydroxycyclohexyl-piperazine 1 g (3.2 mM) of 1-[2-(bis(4-fluorophenyl)-methoxy)ethyl]piperazine was dissolved in 5 ml of cyclohexene oxide and refluxed for 16 h. The solvent was evaporated and the residue dissolved in methylene chloride and treated with charcoal, evaporated and dissolved in ethanol. Addition of 742 mg of maleic acid dissolved in ethanol precipitated white crystals melting at 165°–167° C. and showing H-NMR spectrum in accordance with the dimaleate of the title compound.

NMR-data (DMSO) ppm: 1.1–1.4 (m) 4H; 1.6 (m) 1H; 1.7 (m) 1H; 1.9 (m) 2H, 2.6–3.6 (m) 12H (+H$_2$O); 5.5 (s) 1H; 6.2 (s) 4H; 7.2 (t) 4H; 7.4 (dd) 4H.

| Microanalysis | C | H | N |
|---|---|---|---|
| Calculated for C$_{33}$H$_{39}$N$_2$O$_{10}$F$_2$ | 59.90 | 5.94 | 4.23 |
| Found | 59.36 | 6.28 | 4.26 |
| | 59.03 | 6.03 | 4.41 |

EXAMPLE 16

1-[2-bis-(4-fluorophenyl)-methoxy)-ethyl]-4-(2,3-dihydroxypropyl)piperazine 580 mg (1.7 mM) of 1-[2-(bis-(4-fluorophenyl)-methoxy)ethyl]piperazine and 130 mg (1.7 mM) of freshly distilled glycidol were mixed at room temperature and then heated at 40° C. for 5 min. The reaction mixture was dissolved in 20 ml of acetone and 400 mg of maleic acid was added. A slow crystallization ensued, and after 48 h the precipitate was isolated and recrystallized from 30 ml of hot acetonitrile to produce 712 mg (65%) of the dimaleate salt of the title compound as colourless crystals melting at 152°–154° C. The analytical data were in accordance with the proposed structure.

H-NMR data (DMSO) ppm: 2.6–3.5 (m) 12H (+H$_2$O); 3.5 (m) 2H, 3.8 (m) 1H, 5.3 (broad) 1H; 5.5 (s) 1H; 6.2 (s) 4H; 7.2 (t) 4H; 7.4 (dd) 4H.

| Microanalysis: | C | H | N |
|---|---|---|---|
| Calculated for C$_{30}$H$_{36}$N$_2$O$_{11}$F$_2$ | 56.42 | 5.68 | 4.39 |
| Found | 55.93 | 5.86 | 4.29 |
| | 56.28 | 5.93 | 4.18 |

EXAMPLE 17

1-[2-(bis-(4-fluorophenyl)-methoxy)-ethyl]-4-(3-phenyloxadiazol-5-yl-methyl)piperazine 1.08 g (3.3 mM) of 1-[2-(bis-(4-fluorophenyl)-methoxy)ethyl]piperazine and 0.97 g of 3-phenyl-5-chloromethyl-1,2,4-oxadiazole (prepared according to Chem.Ber. 105 (1972)2825) were dissolved in 5 ml of dry dimethylformamide. 1.4 g of potassium carbonate were added and the mixture was stirred at room temperature overnight. Toluene and water were added, the aqueous phase extracted with toluene, the combined organic phases washed three times with water, treated with charcoal and evaporated in vacuo. The residue was dissolved in 10 ml of ethanol and 0.69 g of maleic acid were added. The precipitate was isolated by filtration and recrystallized from hot acetonitrile to obtain the dimaleate salt of the title compound as colourless crystals melting at 142°–143°. Analytical data were in accordance with the proposed structure.

H-NMR data (DMSO) ppm: 2.6–3.6 (m) 12H (+H$_2$O); 3.7 (m) 2H, 4.1 (s) 2H; 5.6 (s) 1H; 6.2 (s) 4H; 7.2 (t) 4H; 7.4 (dd) 4H; 7.6 (m) 3H; 8.0 (m) 2H.

| Microanalysis: | C | H | N |
|---|---|---|---|
| Calculated for C$_{36}$H$_{36}$N$_4$O$_{10}$F$_2$ | 59.83 | 5.02 | 7.75 |
| Found | 59.73 | 5.03 | 7.56 |
| | 59.92 | 5.07 | 7.62 |

EXAMPLE 18

1-[2-(bis-(4-fluorophenyl)-methoxy)-ethyl]-4-(3-ketobutyl)piperazine

A mixture of 0.7 g (2.1 mM) of 1-[2-(bis-(4-fluorophenyl)-methoxy)-ethyl]piperazine and 150 mg (2.1 mM) of freshly distilled methylvinyl-ketone was stirred at room temperature for 2 h. 30 ml of ethanol and 0.48 g of maleic acid were added, the precipitated salt was isolated by filtration and recrystallized from hot acetonitrile to yield the dimaleate salt of the title compound as colourless crystals melting at 159°–160° C. Analytical data were in accordance with the proposed structure.

H-NMR data (DMSO) ppm: 2.6 (s) 3H; 2.6–3.4 (m) 14H+H20; 3.6 (m) 2H. 5.5 (s) 1H; 6.1 (s) 4H; 7.2 (t) 4H; 7.4 (dd) 4H.

| Microanalysis: | C | H | N |
|---|---|---|---|
| Calculated for C$_{31}$H$_{36}$N$_2$O$_{10}$F$_2$ | 58.67 | 5.72 | 4.42 |
| Found | 58.69 | 5.82 | 4.26 |

EXAMPLE 19

1-[2-(bis-(4-fluorophenyl)-methoxy)-ethyl]-4-(2-hydroxy-3-phenoxy-propyl)piperazine 960 mg (2.9 m) of 1-(2-(bis(4-fluorophenyl)-methoxy) -ethyl)-piperazine was dissolved in 10 ml of 1,2-epoxy-3-phenoxy-propane and warmed at 50° C. for 2 h. The mixture was cooled to 4° C., and a solution of 673 mg (6 mM) of maleic acid in ethanol was added. The precipitate was isolated, redissolved in water and methylene chloride, pH adjusted to 8 and the organic phase was isolated and evaporated. The residue was dissolved in ethanol, 673 mg of maleic acid was added, and the precipitated maleate was isolated and recrystallized from acetonitrile to yield white crystals melting at 164°–165°

C., showing H-NMR spectrum in accordance with the dimaleate salt of the title compound.

NMR-data (DMSO) ppm: 2.6–3.5 (m) 13H (+H₂O); 3.6 (m) 2H; 3.9 (m) 2H; 4.2 (m) 1H; 5.5 (s) 1H; 6.2 (s) 4H; 6.9 (t) 3H; 7.2 (dd) 4H; 7.3 (t) 2H; 7.4 (m) 4H.

| Microanalysis | C | H | N |
|---|---|---|---|
| Calculated for $C_{36}H_{40}N_2O_{11}F_2$ | 60.49 | 5.63 | 3.92 |
| Found | 60.81 | 5.77 | 3.90 |
|  | 60.41 | 5.74 | 3.85 |

EXAMPLE 20

1-[2-(bis-(4-fluorophenyl)-methoxy)-ethyl]-4-(2-hydroxy-5-hexen-1-yl)piperazine 700 mg (2.1 mM) of 1-[2-(bis-(4-fluorophenyl)-methoxy)ethyl]piperazine and 0.24 ml (2.1 mM) of 1,2-epoxy-5hexene were mixed and heated at 50o for 4 h. Another 0.5 ml of epoxyhexene were added together with 10 mg of sodium hydride/oil suspension, and heating continued for 16 h. 15 ml of ethanol were added, and the solution was filtered before adding 490 mg of maleic acid. The precipitate was isolated and recrystallized from 15 ml of hot acetonitrile to yield 640 mg (46%) of colourless crystals melting at 161°–162° C., and with analytical data in accordance with the dimaleate salt of the title compound.

H-NMR data (DMSO) ppm: 1.5 (m) 2H; 2.1–2.2 (m) 2H; 2.6–3.4 (m) 10H+20H; 3.5 (m) 2H; 3.8 (m) 1H; 5.0 (dd) 2H; 5.5 (s) 1H; 5.8 (m) 1H; 6.1 (s) 4H; 7.2 (t) 4H; 7.4 (dd) 4H.

| Microanalysis | C | H | N |
|---|---|---|---|
| Calculated for $C_{33}H_{40}N_2O_{10}F_2$ | 59.80 | 6.08 | 4.22 |
| Found | 59.76 | 6.13 | 4.21 |
|  | 59.75 | 6.14 | 4.32 |

EXAMPLE 21

1-(2-(bis-(4-fluorophenyl)-methoxy)-ethyl)-4-(3-hydroximino-butyl)piperazine 630 mg (1 mM) of 1-(2-(bis-(4-fluorophenyl)-methoxy)-ethyl)-4 -(3-ketobutyl)piperazine (prepared as described in example 19) was suspended in 2 5 ml of ethanol at room temperature. A solution of hydroxylamine hydrochloride in 1 ml of water was added, followed by the dropwise addition of 240 mg of potassium hydroxide dissolved in 1 ml of water. The mixture was heated at reflux for 1 h, the solvent was evaporated, and the residue was dissolved by the addition of 5 ml of water and 5 ml of methylene chloride. The aqueous phase was extracted three times with methylene chloride, and the organic extract was washed with water, dried, and evaporated in vacuo. The residual oil was dissolved in ethanol, and a crude dimaleate salt was precipitated by addition of an ethanolic solution of 417 mg of maleic acid. The crude salt (405 mg) was recrystallized from 50 ml of hot ethanol to yield the dimaleate salt of the title compound as colourless crystals, melting at 161°–162° C. Analytical data were in accordance with the proposed structure. H-NMR spectrum indicated the presence of two stereoisomers in the ratio of 2.5:1.

H-NMR data (DMSO) ppm: 1.75 (s) 2.2H; 1.8 (s) 0.8H; 2.4–3.4 (m) 18H (+H₂O); 5.6 (s) 1H; 6.2 (s) 4H; 7.2 (t) 4H; 7.4 (dd) 4H; 10.5 (s) 1H.

| Microanalysis | C | H | N |
|---|---|---|---|
| Calculated for $C_{31}H_{37}N_3O_{10}F_2$ | 57.31 | 5.74 | 6.47 |
| Found | 57.17 | 5.79 | 6.22 |
|  | 57.25 | 5.80 | 6.22 |

EXAMPLE 22

1-(2-[Bis-(4-fluorophenyl)methoxy]ethyl)-4-(3-diethylphosphonopropyl)piperazine, dimaleate A mixture of 0.997 g (0.003 mol) 1-(2-[bis-(4-fluorophenyl)methoxy]ethyl)piperazine, 1.04 g (0.004 mol) diethyl 3-bromopropylphosphonate, 0.55 g (0.004 mol) dried potassium carbonate and 25 ml 2-butanone was stirred and heated to reflux temperature for 5 h. The reaction mixture was then diluted with 50 ml toluene, washed twice with water and once with brine. The toluene solution was then dried with sodium sulfate and evaporated in vacuo. The oily residue was dissolved in dry diethyl ether and the dimaleate salt precipitated by adding a solution of maleic acid in ether. The crude precipitate was recrystallized from acetonitrile. White crystals, m.p. 146°–47° C. (0.80 g=36%).

NMR (400 MHz) in DMSO-d₆ (ppm): 1.25 (t) 6H; 1.75 (m) 4H; 2.6–3.4 (m) 14H; 3.55 (m) 2H; 4.0 (m) 4H; 5.55 (s) 1H; 6.15 (s) 4H; 7.18 (t) 4H; 7.38 (dd) 4H.

Calculated for $C_{34}H_{45}N_2F_2O_{12}P$: C 54.98, H 6.11 N 3.77%.

Found : C 54.97, H 6.06N 4.34%.

EXAMPLE 23

1-(2-[Bis-(4-fluorophenyl)methoxy]ethyl)-4-(2-ethoxyethyl)piperazine, dimaleate

The title compound was prepared in the same manner as outlined in example 22 from the following ingredients: 0.665 g (0.002 mol) 1-(2-[bis-(4-fluorophenyl)methoxy]-ethyl)piperazine, 0.612 g (0.004 mol) bromoethyl ethyl ether, 0.552 g (0.004 mol) potassium carbonate and 20 ml 2-butanone as solvent. Cream coloured crystals, m.p. 175°–76° C. (0.84 g=66%).

NMR (400 MHz) in DMSO-d₆ (ppm): 1.17 (t) 3H; 2.6–3.4 (m) 14H; 3.47 (q) 2H; 3.55 (m) 2H; 3.60 (m) 2H; 5.52 (s) 1H; 6.15 (s) 4H; 7.18 (t) 4H; 7.40 (dd) 4H.

Calculated for $C_{31}H_{38}N_2F_2O_{10}$: C 58.48, H 6.02,N 4.40%.

Found: C 58.12, H 6.10,N 4.53%.

In the same manner was prepared:

1-(2-[Bis-(4-fluorophenyl)methoxy]ethyl)-4-[2-(2-ethoxyethoxy)ethyl]piperazine, dimaleate White crystals, m.p. 161°–162° C.

NMR (400 MHz) in DMSO-d₆ (ppm): 1.10 (t) 3H; 2.6–3.3 (m) 14H; 3.40 (q) 2H; 3.50 (m) 2H; 3.55 (m) 2H; 3.65 (m) 2H; 5.52 (s) 1H; 6.15 (s) 4H; 7.20 (t) 4H; 7.40 (dd) 4H.

Calculated for $C_{33}H_{42}N_2F_2O_{11}$: C 58.23, H 6.22,N 4.12%.

Found: C 58.59, H 6.42,N 4.16%.

We claim:

1. A compound of formula I:

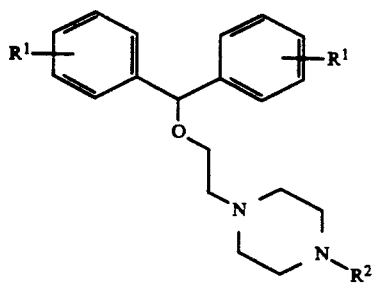

(I)

wherein

R¹ is halogen, methoxy, $C_{1-6}$-alkyl or trifluoromethyl; and

R² is straight or branched $C_{1-8}$-alkyl or $C_{3-8}$-alkenyl, each of which may be optionally substituted at a carbon atom other than position 1 by hydroxy, keto or hydroxyimino and each of which is terminally substituted with phosphono, thienyl, oxazolyl, isoxazolyl or oxadiazolyl, each of which may be optionally substituted by $C_{1-6}$-alkyl or phenyl; or a pharmaceutically acceptable salt thereof.

2. The compound according to claim 1, wherein R¹ is fluorine attached to the four position of the phenyl groups.

3. The compound according to claim 1 which is

1-[2-(bis-(4-fluorophenyl)methoxy)ethyl]-4-[3-(3-thienyl)propenyl]piperzine;

1-[2-(bis-(4-fluorophenyl)methoxy)ethyl]-4-[4-oxo-4-(2-thienyl)butyl]piperazine;

1-[2-(bis-(4-fluorophenyl)methoxy)ethyl]-4-[4-hydroxy-4-(2-thienyl)butyl]piperazine; or a pharmaceutically acceptable salt thereof.

4. A compound of formula I:

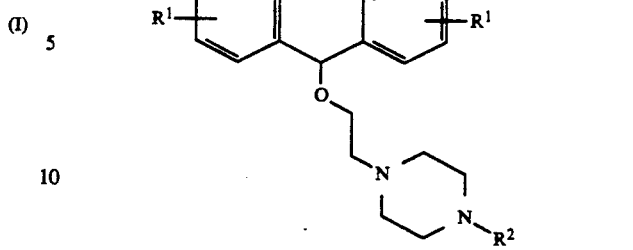

(I)

wherein

R¹ is fluorine attached to the four position of each phenyl group; and

R² is straight or branched $C_{4-8}$-alkyl which is terminally substituted with cyano; or a pharmaceutically acceptable salt thereof.

5. The compound according to claim 4 which is

1-[2-(bis-(4-fluorophenyl)methoxy)ethyl]-4-(4-cyanobutyl)piperazine;

1-[2-(bis-(4-fluorophenyl)methoxy)ethyl]-4-(5-cyanopentyl)piperazine;

1-[2-(bis-(4-fluorophenyl)methoxy)ethyl]-4-(7-cyanoheptyl)piperazine; or a pharmaceutically acceptable salt thereof.

6. A pharmaceutical composition, comprising an effective amount of a compound according to claim 1 and a pharmaceutically acceptable carrier.

7. The pharmaceutical composition according to claim 6 in the form of an oral dosage unit containing about 50–200 mg of the active compound.

8. A pharmaceutical composition, comprising an effective amount of a compound according to claim 4 and a pharmaceutically acceptable carrier.

9. The pharmaceutical composition according to claim 8 in the form of an oral dosage unit containing about 50–200 mg of the active compound.

10. A method of treating a central nervous system ailment in which a dopaminergic deficit is implicated in a subject in need thereof, comprising administering an effective amount of a compound of claim 1.

11. A method of treating a central nervous system ailment in which a dopaminergic deficit is implicated in a subject in need thereof, comprising administering an effective amount of a compound of claim 4.

12. A method of treating a central nervous system ailment in which a dopaminergic deficit is implicated in a subject in need thereof, comprising administering a pharmaceutical composition according to claim 6.

13. A method of treating a central nervous system ailment in which a dopaminergic deficit is implicated in a subject in need thereof, comprising administering a pharmaceutical composition according to claim 8.

14. The method according to claim 10, wherein the central nervous system ailment is depression or Parkinson's disease.

15. The method according to claim 12, wherein the central nervous system ailment is depression or Parkinson's disease.

* * * * *